United States Patent [19]

Login

[11] Patent Number: 4,812,263

[45] Date of Patent: Mar. 14, 1989

[54] BIS-QUATERNARY AMMONIUM COMPOUNDS

[75] Inventor: Robert B. Login, Oakland, N.J.

[73] Assignee: PPG Industries, Inc., Pittsburgh, Pa.

[21] Appl. No.: 173,834

[22] Filed: Mar. 28, 1988

Related U.S. Application Data

[63] Continuation-in-part of Ser. No. 909,430, Aug. 22, 1986, Pat. No. 4,734,277, which is a continuation-in-part of Ser. No. 677,738, Dec. 3, 1984, abandoned, which is a continuation-in-part of Ser. No. 519,129, Aug. 1, 1983, abandoned.

[51] Int. Cl.$^4$ .................... C07C 85/00; C07C 103/34; C07C 187/30; C09F 5/00
[52] U.S. Cl. ............................ 260/404.5 Q; 564/197; 564/292; 564/295; 564/296
[58] Field of Search ................... 564/295; 260/404.5 Q

[56] References Cited

U.S. PATENT DOCUMENTS

| | | | |
|---|---|---|---|
| 2,878,144 | 3/1959 | Conbere et al. | 260/404.5 Q |
| 2,878,273 | 3/1959 | Conbere et al. | 260/404.5 Q |
| 2,944,902 | 7/1960 | Carroll et al. | 96/107 |
| 3,349,032 | 10/1967 | Krieg | 252/8.55 |
| 3,642,663 | 7/1972 | Greer | 252/500 |
| 3,954,633 | 5/1976 | Dollinger et al. | 252/8.8 |
| 4,110,263 | 8/1978 | Lindemann et al. | 252/545 |
| 4,181,634 | 1/1980 | Kennedy et al. | 252/545 |
| 4,480,126 | 10/1984 | Rutzen | 564/292 |
| 4,734,277 | 3/1988 | Login | 424/70 |

OTHER PUBLICATIONS

"Quaternizations of Triethylamine and Triethanolamine with Epichlorohydrin" by John B. McKelvey et al, I&EC Product Research and Development, vol. 6, No. 2, Jun. 1967, pp. 115–120.

Primary Examiner—Dale R. Ore
Attorney, Agent, or Firm—Irwin M. Stein

[57] ABSTRACT

Described are bis-quaternary ammonium compounds of 2-hydroxypropylene, e.g., 2-hydroxy propylene-1,3-bis(dimethyl stearyl ammonium chloride).

7 Claims, No Drawings

BIS-QUATERNARY AMMONIUM COMPOUNDS

CROSS-REFERENCE TO RELATED APPLICATIONS

This application is a continuation-in-part of my U.S. patent application Ser. No. 909,430, filed Aug. 22, 1986, now U.S. Pat. No. 4,734,277 which in turn is a continuation-in-part of my U.S. patent application No. 677,738, filed Dec. 3, 1984, now abandoned, which in turn is a continuation-in-part of my U.S. patent application Ser. No. 519,129, filed Aug. 1, 1983, now abandoned.

DESCRIPTION OF THE INVENTION

The present invention relates to a process for preparing certain bis-quaternary ammonium compounds and to mixtures thereof. The present invention also relates to improved hair conditioners, skin lotions and other similar cosmetic compositions. Further, the present invention relates to certain novel bis-quaternary ammonium compounds.

Several examples of bis-quaternary or poly-quaternary ammonium compounds have appeared in the patent and trade literature. U.S. Pat. No. 2,129,264 describes the condensation of "glycerol-di-chlorhydrine" with a tallow dimethyl amine to form a "di-quaternary" ammonium salt. U.S. Pat. No. 2,944,902 describes the conversion of polyethylene glycols with methanesulfonyl chloride to the corresponding bis-ester. Condensation of the bis-ester with a tertiary amine result in the bis-quaternary ammonium salt. U.S. Pat. No. 3,349,032 describes the use of alkylene dihalides or the conversion of bis-tertiary amines with monomeric alkylating agents to bis-quaternary ammonium compounds. U.S. Pat. No. 3,954,633 illustrates the quaternization of tertiary fatty diamines which are prepared from fatty amines by the cyandethylation route. U.S. Pat. Nos. 4,110,263 and 4,181,634 describe the conversion of polyalkylene glycols into bis-$\alpha,\omega$-bromoderivatives with phosphorus tribromide and subsequent conversion into the desired bis-quaternary ammonium bromide.

Epichlorohydrin has been employed in a variety of reactions designed to generate quaternary ammonium compounds. For example, U.S. Pat. No. 2,129,264 describes the reaction of fatty tertiary amines and epichlorohydrin to afford mono-quaternary ammonium derivatives. It is also known that secondary amines will condense with epichlorohydrin to form polymeric quaternary ammonium compounds.

Recently, a paper presented before the Society of Cosmetic Chemists (Robert J. Verdicchio, annual meeting, May 13, 1982, Memphis, Tenn.) describes the exceptional affect of certain bis-quaternary ammonium salts on the eye irritation of various cosmetic detergent formulations. It has been shown that the described "bis-quats" act as counter irritants. U.S. Pat. Nos. 4,110,263 and 4,181,634 describe this effect in greater detail.

The present invention is directed to a process for the direct synthesis of bis-quaternary ammonium compounds of which 2-hydroxypropylene-bis-1,3-(dimethyl stearyl ammonium chloride) is an example. The process involves as a first step contacting a tertiary amine with a suitable amount of neutralizing acid, such as hydrochloric acid, whereby about half of the tertiary amine is neutralized, thereby producing a first solution with approximately equimolar concentrations of tertiary amine and tertiary amine salt. The process further involves as a second step contacting at an elevated temperature the resulting first solution with an approximately equimolar amount of a suitable epoxide, such as epichlorohydrin, such that approximately equimolar amounts of tertiary amine, tertiary amine salt and epoxide are used in the second step, thereby to produce, for example, 2 hydroxypropylene-bis-1,3 -(dimethyl stearyl ammonium chloride) in almost stoichiometric yields. Modifications of the process are also disclosed. The resulting bis-quaternary ammonium compounds, particularly those in which R in equation I is a $C_{12}$–$C_{26}$ alkyl, have utility as an additive to cosmetics, such as a hair conditioner, whereby a softer feel and better control of the hair is obtained.

DETAILED DESCRIPTION OF THE INVENTION

Schematically, the present process of this invention can be visualized by the following reaction steps:

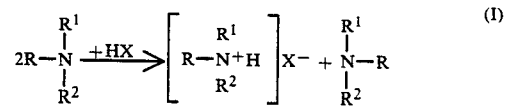

wherein R, $R^1$ and $R^2$ are defined hereinafter and wherein HX is selected from a neutralizing acid in which, for example, X is F, Cl, Br, $NO_3$, $CH_3SO_3$, and $Ch_3C_6H_4SO_3$. A mixture of different neutralizing acids may be used. The second reaction step can be written,

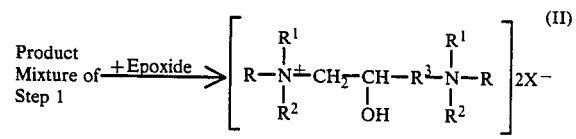

wherein R, $R^1$, $R^2$ and $R^3$ each are selected from the group consisting of alkyl, alkylamidoalkyl, arylalkyl, aryl, alkoxy, alkenyl, hydroxyalkyl, and carboxyalkyl, each having 1–28 carbon atoms and X is a negative radical or a radical obtained from the neutralizing acid and/or the epoxide. The epoxide used in equation II can be represented by the following graphic formula or structure,

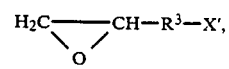

wherein X' is a negative radical which is either the same or different from the anion, X, of the neutralizing acid. Preferred epoxides are epihalohydrins of which epichlorohydrin and epibromohydrin are most preferred. Mixtures of various epoxides can be used.

Step I of the process, which involves contacting the tertiary amine having the aforementioned structure with an amount of nautralizing acid whereby about half of the tertiary amine is neutralized, produces a solution with approximately equimolar concentrations of tertiary amine and tertiary amine salt. Step II of the process involves contacting the resulting product solution of Step I with an approximately equimolar amount (based on the tertiary amine or tertiary amine salt in the product solution) of an epoxide represented by the aforementioned graphic formula so that approximately equimolar amounts of tertiary amine, tertiary amine salt and epoxide are used.

A consideration of the chemistry of steps I and II revolves around the reactivity of the selected tertiary amine. It must be a strong enough nucleophile to be readily alkylated. When the R groups of equation I are aliphatic and contain no electron withdrawing groups or excessive steric hindrance, the reaction proceeds readily through steps I and II. Examples of preferred reactive tertiary amines are fatty di($C_1$-$C_4$)alkyl, e.g., fatty dimethyl, amine compounds. These are represented, for example, as follows:

R—N(R')$_2$, e.g., R—N(CH$_3$)$_2$ and $$R-\overset{O}{\underset{\|}{C}}-NH(CH_2)_xN(R')_2,$$

wherein x is an integer of from 1 to 6, R is an alkyl group containing from 1 to 28 carbon atoms, preferably 12 to 26 carbon atoms, more preferably 18 to 22 carbon atoms, and R' is a $C_1$-$C_4$ alkyl, preferably methyl.

The fatty dialkylamines, e.g., R—NR$^1$R$^2$, may be prepared by the reductive amination of fatty acids followed by subsequent conversion to the tertiary amines with formaldehyde and hydrogen in the presence of a catalyst such as Raney Nickel; or, by the conversation of alpha olefins to their bromo derivatives, which are subsequently condensed with secondary amines; or, by the direct conversion of fatty alcohols in to presence of secondary amines and a catalyst.

The alkyl amidoamines are readily prepared from fatty acids and dimethylaminopropylamine through a condensation reaction. Those skilled in the art will realize that fatty esters, acid chlorides, anhydrides and so forth will also produce amidoamines.

If amines are chosen that are difficult to alkylate with, for example, benzyl chloride, then it is possible such amines will fail to perform in this reaction. The chemistry of benzylation of tertiary amines is well known; therefore, those skilled in the art of quaternization can determine whether or not a candidate tertiary amine can be quaternized by benzyl chloride or by the instant invention without undue effort.

The monofunctional acid used to neutralize one half of the tertiary amine functionality must be selected from acids that form counter ions that will not compete with the said tertiary amine upon subsequent alkylation. For example, acetic acid would not be as ideal as hydrochloric acid because the acetate ion is a much better nucleophile than the chloride ion. Therefore, if the acetate ion was added to the halohydrin or a reactive intermediate, it would prevent conversion to the quaternary compound.

Suitable neutralizing acids react with the tertiary amine to afford only neutralization. Obviously, acids that cause oxidation or reduction would not be suitable if they destroyed the nature of the other reactants.

Suitable neutralizing acids therefore may be experimentally determined without undue effort by actually trying them in the instant invention. for example, it is known that phosphoric and boric acids or their salts can readily add to epichlorohydrin. Therefore, utility of such acids is questionable. Hydrochloric and methane sulfonic acids, for example, are acceptable. Other acids that will also function acceptably can be identified according to the above directions.

It is preferred to neutralize about one half of the tertiary amine functionality; otherwise conversion to the bis-quat with the epoxide, e.g., epichlorohydrin (ECH), will not be complete. Either the chlorohydrin (A) or the glycidyl ether (B) would predominate. The glycidyl ether may hydrolyze to the diol (C) with termination of conversion to the bis-quat. These proposed reaction mechanism may be illustrated as follows:

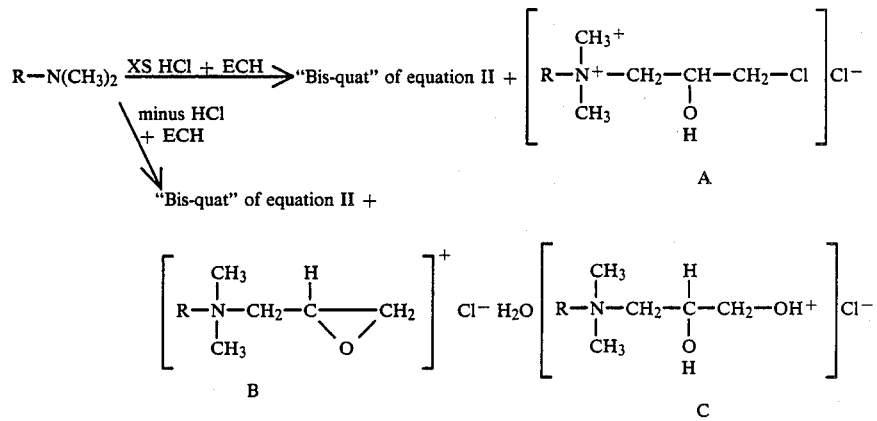

Many of the "bis-quats" formed from fatty dimethyl amines are viscosity builders in water. The $C_{18}$ analog will gel water at as low a concentration as 1 percent. The reason for this could be the interaction of the two long fatty chains which can form a crosslinked (by Van der Waals forces) three dimensional structure. As expected, monomeric ingredients compatible with the "bis-quats" can raadily reduce the viscosity of such mixtures. Therefore, it is preferred to prepare the "bis-quats" in water, a semi-polar liquid or in a semi-polar liquid-water mixture. Examples of semi-polar liquids include the alcohols such as methanol, ethanol, propanol, isopropanol, butanol, isobutanol, ethylene glycol and propylene glycol. Other alcohols and other classes of solvents compatible with water may be employed. Thus, a general solvent used is one in which the amine, the neutralized amine, the epoxide, and the bis-quaternary ammonium product are soluble. Those skilled in the art of carrying out quaternizations realize that the list of suitable solvents and solvent combinations can be determined experimentally without undue effort.

As in many quaternization reactions some hydrolysis will occur; therefore, although all ingredients are exactly weighed and charged, there is a need at the end of the reaction to adjust the preparations into the required specifications by small additions of epoxide and/or neutralizing acid. If mischarged and too much hydrolysis has occurred to form the di-hydroxy derivative (C), then the preparation cannot be brought into specifications; however, if the chlorohydrin (A) predominates, then more tertiary amine can be added to complete the reaction.

If a mixed "bis-quat" is desired, one tertiary amine can be selectively converted into the chlorohydrin (A) followed by condensation with the other tertiary amine. This procedure requires another step but can be carried out in the sama reactor. A more detailed analysis to determine conversion to the chlorohydrin (A) is required; however, such mixed products are very desirable because of the ability to design duo-function quaternaries.

For example, a mixed "bis-quat" of lauryl and stearyl dimethyl amines would afford a product in which one quat, the stearyl based compound, would afford substantivity to hair or fiber while the lauryl based compound would afford a modest measure of germicidal activity. A greater level of germicidal activity might be expected from a decyl or octyl based dimethylamine or greater softening and substantivity would be expected from a larger alkyl group than stearyl.

Simply mixing the amines from the beginning of the process would result in a statistical distribution of the single amine generated "bis-quats" and a portion of the mixed "bis-quats". If a majority of the mixed "bis-quats" is required, then the appropriate chlorohydrin (A) will have to be formed first. Such a refinement does not however require more equipment for manufacture. It is simply two processing steps in one reactor.

Thus, the present invention contemplates a process for preparing bis-quaternary ammonium compounds involving the following steps. A tertiary amine, as defined herein, is contacted with an amount of a neutralizing acid, as defined herein, which will neutralize about half of the tertiary amine. While neutralizing about one-half of the tertiary amine is preferred, other amounts of neutralization near to the one-half value are within the scope of the present invention. A preferred method of contacting the tertiary amine with neutralizing acid is by dissolving the tertiary amine in a suitable solvent as defined herein.

The resulting mixture containing the neutralized tertiary amine is contacted with a suitable epoxide as defined herein. If this portion of the reaction is performed with a solvent, then the contacting temperature is from about 20° C. to 150° C. A preferred temperature range is from about 50° C. to 100° C. Generally, the epoxide is slowly added to the resulting mixture.

Another embodiment of the present invention is a process for preparing a mixture of bis-quaternary ammonium compounds involving the following. A tertiary amine,

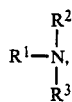

wherein $R^1$, $R^2$ and $R^3$ each are selected from the group consisting of alkyl, alkylamidoalkyl, arylalkyl, aryl, alkoxy, alkenyl, hydroxyalkyl and carboxyalkyl, each having 1-28 carbon atoms, is contacted with an amount of neutralizing acid, as defined herein, which will neutralize a substantial portion of the tertiary amine. By substantial is meant that which is desirable depending on the desired composition of the final product. A preferred embodiment is that essentially all of the tertiary amine is neutralized. After the neutralization reaction, the resulting neutralized mixture is contacted with an epoxide having the structure

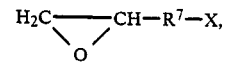

wherein both $R^7$ and X are as defined herein. The contacting temperature of the epoxide and neutralized mixture is in the range of from about 20° C. to about 150° C., preferably 50° C. to 100° C. The resulting product of the epoxide and neutralized mixture is then subsequently contacted with a tertiary amine

wherein $R^6$, $R^4$ and $R^5$ each are selected from the group consisting of alkyl, alkylamidoalkyl, arylalkyl, aryl, alkoxy, alkenyl, hydroxyalkyl and carboxyalkyl, each having 1-28 carbon atoms and at least one of the groups, $R^4$, $R^5$ and $R^6$ is different from one of the R groups of the tertiary amine contacted with the neutralizing acid. The resulting products from the process for preparing a mixture of bis-ammonium compounds have the following graphic formula structure:

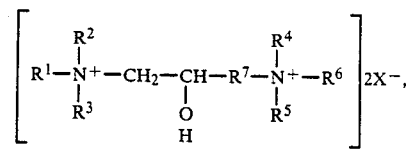

wherein X is a negative radical or radicals obtained from the neutralizing acid and epoxida. Thus, for example, if nitric acid is used to neutralize the amine and an epoxide having a chloride is used to react with the neutralized amine, then the X anion radicals in the above structure are $NO_3$ and Cl. However, if hydrochloric acid is used to neutralize the amine in place of the nitric acid, then the X radical is Cl.

With either of the above described processes, the novel bis-quaternary ammonium compound has the following structure:

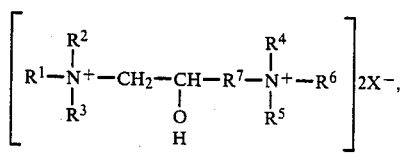

wherein $R^1$, $R^2$, $R^3$, $R^4$, $R^5$, $R^6$ and $R^7$ each are selected from the group consisting of alkyl, alkylamidoalkyl arylalkyl, aryl, hydroxyalkyl and carboxyalkyl each having 1-28 carbon atoms and X is a negative radical anion as defined herein. The preferred compounds are wherein $R^7$ has 2-28 carbon atoms.

The "bis-quats" can be considered as useful in many applications. For example, as softeners for various textile and laundry applications, "bis-quats" of stearyl dimethylamine and mixed "bis-quats" of lauryl and stearyl dimethylamines were found to afford similar feel (hand) and acceptable scorch resistance as compared to a variety of commercial softeners. In addition, the phenol coefficients for bacteriocidal effectiveness suggest that the 12/18 "bis-quat" could also function as a bacteriostat, thereby affording the key ingredient in softener/sanitizer formulations. Example 4 illustrates this work.

Hair conditioning in the after shampoo hair care market is another application for the "bis-quats". Preliminary screening on human hair swatches indicate positive conditioning results with the stearyl based "bis-quat". Other screening tests show that $C_{12}$–$C_{26}$ dimethyl bis-quats provide good substantivity to fabrics, and indicate good results would be obtained for human hair.

Hair in contact with water usually acquires a negative charge. However, when a cationic material is deposited onto it, the hair becomes positively charged. The positively charged hair will attract and hold on its surface a negatively charged macro polyanion, such as the polyanion of red dye molecules used t test for substantivity of a particular cationic material. The hair will thus acquire a substantive red color. The intensity of the red color on the hair, e.g., a test hair swatch, is a function of the extent of adsorption of the dye, which in turn is a function of the cationic charge density on the hair, which again is a function of the extent of deposition and substantivity of the particular cationic resin on the hair.

The "bis-quats" of the present invention are also useful as antistats, cationic emulsifiers, ore-flotation agents, dye bath assistants, and pigment dispersants, as well as other applications.

The following examples illustrate the invention, but are not to be construed as limiting:

EXAMPLE 1

(2-hydroxypropylene-bis-1,3-dimethyl stearyl ammonium chloride)

A 12 liter round bottom flask equipped with a mechanical stirrer, thermometer, reflux condenser and dripping funnel was charged with 2,824 grams of stearyl dimethyl amine (equivalent weight 297); 1,610 grams of isopropanol and 1,610 grams of deionized water. With agitation, 406 grams of concentrated (37.2%) hydrochloric acid was slowly added. After 15 minutes, a sample was removed and analyzed for free amine nd amine-hydrochloride. In this particular case, employing acid/base titration, a difference of 0.15 meq/g in favor of the amine was observed. Neutralization of half of the residual free amine was desired. This required an additional 51 grams of concentrated hydrochloric acid.

Epichlorohydrin (438 grams) was charged into a pressure equalizing dropping funnel; the mixture in the flask was heated to 55° C. and the epichlorohydrin was added dropwise to the mixture over a 1.5 hour period. The temperature rose through a modest exotherm to 85° C. Analysis at this point indicated 3.2% amine hydrochloride and 5.2% free amine. On standing overnight, analysis indicated 1.98% amine hydrochloride and 2.5% free amine. The amine hydrochloride value was employed to calculate the addition of further epichlorohydrin. A total of 39 more grams of epichlorohydrin were added dropwise at 70° C. and the mixture agitated an additional four hours. Final analysis was as follows:
- % Actives (Epton Titration): 46.9 (Equivalent weight 361.5)
- % Free Amine: 0.83 (Equivalent weight 297)
- % Amine HCl: 0.53 (Equivalent weight 333.5)
- % Solids (2 hrs., 150° C.): 51.1
- pH (1% aqueous soln): 5.1

Upon standing at ambient temperatures, the clear yellow liquid product solidified into a white paste.

EXAMPLE 2

(2-hydroxypropylene-bis-1,3-dimethyl lauryl ammonium chloride)

A three liter round bottom flask equipped as reported in Example 1 was charged with 461 grams of lauryl dimethyl amine (equivalent weight 218), 299 grams of isopropanol and 233 grams of deionized water. With stirring, 96.8 grams of hydrochloric acid were slowly added. Analysis by acid-base titration indicated an equivalent of free amine and amine hydrochloride to be present. The mixture was heated to 80° C. and 98 grams of epichlorohydrin were slowly charged over an hour and a half. After 8–10 hours of mixing at 80° C., analysis indicated:
- % Solids (105° C., 1.5 hrs.): 52.0
- % Actives (Epton Titration; equivalent weight 265): 43.5
- % Free Amine (equivalent weight 218): 0.88
- % Amine Hydrochloride (equivalent weight 254.4): 0.32

EXAMPLE 3

(Mixed bis-quat of Lauryl dimethyl amine and Stearyl dimethyl amine)

A three liter round bottom flask equipped as reported in Example 1 was charged with 422 grams of lauryl dimethyl amine, 563 grams of isopropanol alcohol and 501 grams of deionized water. With agitation, 185 grams of concentrated 37% hydrochloric acid was added. This addition raised the temperature to 80° C. At this point, 175 grams of epichlorohydrin was added over a ½ hour period. Analysis indicated acceptable conversion to the quat-halohydrin chloride salt. To this mixture was added 577 grams of stearyl dimethyl amine. The mixture was reacted at 80° C. for 8–10 hours. In order to bring the free amine and amine hydrochloride into specification, an additional 15 grams of epichlorohydrin was required. Final analysis was as follows:
- % Solids (105° C., 1.5 hrs.): 52.9
- % Actives (Epton Titration; equivalent weight 319.5): 46.8
- % Amine Hydrochloride (equivalent weight 291.5): 0.9
- % Free Amine (equivalent weight 255): 1.1
- pH (10 % Aqueous soln): 6.8

EXAMPLE 4

(2-hydroxypropylene-bis-1,3-stearamidopropyldimethyl- ammonium chloride)

A three liter round bottom flask equipped as reported in Example 1 was charged with 394 grams of stearamidopropyl dimethyl amine equivalent weight 365), 500 grams isopropanol and 500 grams deionized water. To this mixture, was added with agitation 54.9 grams of concentrated hydrochloric acid. The mixture was heated to 80° C. and 103.9 grams of epichlorohydrin was added over a ½ hour period. After 8-10 hours at 80° C., the product analyzed as follows:
- % Solids (105° C., 1.5 hrs.): 34.1
- % Actives (Epton Titration; equivalent weight 429.5): 30.1
- % Amine Hydrochloride (equivalent weight 401.5): 0.1
- % Free Amine (equivalent weight 365): 0.3

EXAMPLE 5

The products of Examples 1-3 were evaluated as germicides by the AOAC Phenol Coefficient method against *Staphylococcus aureus* and *Pseudomonas aeruginosa* with the following results:

| Product, Example | S. aureus | Phenol Coeff. P. aeruginosa |
|---|---|---|
| 1 | 45 | 17 |
| 2 | 500 | 133 |
| 3 | 338 | 71 |

Examples 1 and 3 were further evaluated against a variety of textile dye bath softeners and Downy ® fabric softener on acrylic and polycotton fabric at equal add on concentrations. Subject results reviewed by a panel of 3-4 individuals identified the products of Examples 1 and 3 to be as effective as the commercial products in softening ability.

EXAMPLE 6

A hair conditioner was prepared. The composition was as follows:

| Ingredient | % By Weight |
|---|---|
| 2-hydroxypropylene-bis-1, 3-(dimethyl stearylammonium chloride) | 5.0 |
| cetyl alcohol | 2.0 |
| hydroxyethyl cellulose | 2.0 |
| preservative | 0.2 |
| water | Balance |
| Total | 100% |

The procedure used to prepare the hair conditioner was as follows. The hydroxyethyl cellulose was slowly added to cold water with agitation. After mixing, the resulting mixture was heated to from about 80° C.-90° C. The bis-quat compound was added to the heated mixture. The cetyl alcohol was melted and added to the heated mixture. The pH of the resulting mixture was adjusted within the range of from 5.0-6.0 with a 50% solution of citric acid. Perfume may be added as desired.

The above composition was panel tested versus an equivalent formula containing the most widely utilized hair conditioner ingredient, stearalkonium chloride. The formula was adjusted to contain an equal level of active conditioner. The results are as follows:

| | % Preference for Above Composition | % Preference for Stearalkonium Chloride | % Equal |
|---|---|---|---|
| Overall | 83 | 8 | 9 |
| Wet Combining | 44 | 0 | 56 |
| Dry Combining | 22 | 0 | 78 |
| Body | 40 | 30 | 30 |
| Flyaway | 60 | 0 | 40 |
| Luster | 67 | 0 | 33 |
| Feel | 80 | 10 | 10 |

The comment most often received was that the above composition resulted in a softer feel and better control of the air than with the stearalkonium chloride.

EXAMPLE 7

A skin lotion was prepared. The composition was as follows:

| INGREDIENTS | % BY WEIGHT |
|---|---|
| PORTION A | |
| Glycerol Monostearate | 2.00 |
| Cetyl Alcohol | 0.25 |
| Stearyl Alcohol | 0.25 |
| Isopropyl Palmitate | 4.00 |
| Lanolin | 2.00 |
| Mineral Oil | 8.00 |
| PORTION B | |
| Stearamine Oxide | 10.00 |
| 2 hydroxypropylene-bis-1, 3-(dimethyl stearylammonium chloride) | 4.00 |
| Water | 71.00 |
| PORTION C | |
| Perfume (if desired) | 0.20 |

The procedure used to prepare the skin lotion was as follows. The ingredients of Portion A were blended together and heated to 70° C. with agitation. Each of the ingredients of Portion B were heated separately oo 75° C. The stearamine oxide and water were mixed together and the pH of the resulting mixture was adjusted to from 5.5 to 6.0 by the addition of citric acid. Portion B was blended into Portion A with rapid agitation and then cooled to 35° C. with stirring, at which temperature the perfume, if desired, is added.

The above formula was panel tested versus the same composition without the bis-quat compound. The addition of the latter resulted in better initial and after feel.

The above composition was also panel tested versus a leading national brand. The composition containing the bis-compound was overwhelmingly preferred.

Other "bis-quats" may be prepared in a similar manner as described in Examples 1, 2, 3 and 4 using other epoxides and other tertiary amines with equally good yields.

EXAMPLE 8

(2-Hydroxy Propylene-bis-1,3-trimethyl ammonium chloride)

Into a 1 liter three necked flask, equipped with an addition funnel and condenser, were charged 150 grams of water, 150 grams of ethanol and 211.8 grams of 25% trimethyl amine in water (0.897 mole). 46.8 grams of reagent grade hydrochloric acid (0.449 mole) were added slowly to the flask by means of the addition funnel. The temperature of the reaction mixture rose to 30° C. during the hydrochloric acid addition and was maintained there for an hour while stirring the mixture. Analysis of the resulting solution indicated the presence of 0.79 meq/g free amine and 0.84 meq/g amine hydrochloride. 41.4 grams (0.448 moles of epichlorohydrin were added slowly to the flask by means of the addition funnel. The exotherm resulting from the initial addition of epichlorohydrin raised the temperature to 70° C. rapidly and it was maintained there by controlling the rate of epichlorohydrin addition. When all of the epichlorohydrin had been added, the temperature of the reaction mixture was raised to 85° C. and held there for two hours. Analysis of the reaction mass indicated the presence of 0.041 meq/g free amine and 0.036 meq/g amine hydrochloride. It was heated and mixed for an additional 2 hours. Further analysis yielded the following results:
   0.004 meq/g free amine
   0.068 meq/g amine hydrochloride
   1.45 meq/g quaternary chlorid
This analysis translates to 0.725 mmole/g or 19.9% quaternary using a molecular weight of 247.

EXAMPLE 9

Preparation of 2-hydroxy propylene-bis-1,3-(dimethyl octyl ammonium chloride)

A three liter flask equipped with an additon funnel was charged with 506.4 grams (3.22 moles) of dimethyl octyl amine, 345 grams of isopropanol and 345 grams of water. 157.6 grams (1.60 moles) of 37% hydrochloric acid were added slowly to the flask through the addition funnel while mixing the contents of the flask. The resulting exotherm brought the temperature in the flask to 44° C.

The temperature of the reaction mixture was increased to 72° C. and 147 grams (1.59 moles) of epichlorohydrin added slowly to the flask through the addition funnel. The temperature of the reaction mixture rose to 84° C. and was maintainad there by regulating the rate of epichlorohydrin addition. The reaction mixture was maintained at 84° C. for two hours, cooled and then analyzed. 4.8 grams of hydrochloric acid were added to adjust the pH of the reaction mixture. The final analysis was:

| | |
|---|---|
| % Active product (molecular weight 223.9) | 46.0 |
| % Amine Hydrochloride (molecular weight 195.9) | 1.70 |
| % Free Amine (molecular weight 159.4) | 0.06 |
| pH, 1% aqueous | 5.0 |
| % Solids (1 g, 105° C., 1½ hour) | 50.6 |

EXAMPLE 10

Preparation of 2-hydroxy propylene-bis-1,3-(dimethyl lauryl ammonium chloride)

A three liter three-necked flask equipped with an addition funnel was charged with 583 grams (2.73 moles) of lauryl dimethyl amine, 330 grams of water and 330 grams of ethanol. With agitation, 133 grams (1.35 moles) of 37% hydrochloric acid was added to produce an equipmolar solution of lauryl dimethyl amine and lauryl dimethyl amine hydrochloride. The resulting exotherm brought the temperature to 60° C. 114.6 grams (1.24 moles) of epichlorohydrin was slowly added to the flask throught the addition funnel. The exothermic reaction brought the temperature of the contents of the flask to 71° C. The temperature of the reaction mixture was increased to 90° C. and maintained there for five hours.

The reaction mixture was analyzed and 90 additional grams (0.10 mole) of epichlorohydrin were added to adjust the free amine and amine hydrochloride downward. The reaction mixture was heated to 85° C. for several more hours and then analyzed. The pH and solids were adjusted with 2.5 grams of hydrochloric acid and 40 grams of water respectively. The final analysis was:

| | |
|---|---|
| % Actives (equivalent weight 277.5) | 45.5 |
| % Amine Hydrochloride (molecular weight 249.5) | 1.72 |
| % Free amine (molecular weight 213) | 0.84 |
| pH | 5.6 |
| % Solids | 50.1 |

EXAMPLE 11

Preparation of 2-hydroxy propylene-bis-1,3-(dimethyl stearyl ammonium chloride)

A 2000 gallon glass lined tank equipped with a steam jacket and stainless steel condeser set up for reflux was charged with 4884 pounds (7466 moles) of stearyl dimethyl amine, 2784 pounds of ethanol and 334 gallons of filtered water. With agitation, 720 pounds (3314 moles) of reagent grade hydrochloric acid was added to the tank. Analysis of the tank contents indicated a 0.642 meq/g of amine hydrochloride and 0.832 meq/g free amine. 90 additional pounds (414 moles) of hydrochloric acid were added to the tank, which brought the amine hydrochloride to 0.749 meq/g and free amine to 0.745 meq/g. The reaction mass was heated to 175° F. (79.4° C.) and 700 pounds (3436 moles) of epichlorohydrin was added to the tank over 30 minutes. The reaction mass was held at 180° F. (82° C.) for four hours and then sampled. Based on such analysis, 170 pounds (834 moles) of epichlorohydrin, 60 pounds (92 moles) of stearyl dimethyl amine, 280 pounds of ethanol and 33 gallons of water were added to the tank. The final analysis was:

| | |
|---|---|
| % Actives (equivalent weight 361.5) | 45.1 |
| % Amine Hydrochloride (molecular weight 333.5) | 0.69 |
| % Free Amine (molecular weight 297) | 1.14 |
| % Solids | 49.9 |
| pH, 1% | 5.6 |

EXAMPLE 12

Preparation of 2-hydroxy propylene-bis-1,3-(dimethyl dicosyl ammonium chloride)

A three liter three-necked flask equipped with an addition funnel was charged with 643.5 grams (1.82 moles) of docosyl dimethyl amine, 321.5 grams of ethanol and 321.5 grams of water. This mixture was heated to 60° C. and 86.2 grams (0.87 mole) of hydrochloric acid was added slowly to the flask over a period of 1½hours. This yielded a reaction solution of 0.677 meq/g of free amine and 0.645 meq/g amine hydrochloride. 2.2 grams (0.02 mole) of additional hydrochloric acid were added to the flask to bring the quantities of free amine and amine hydrochloride to 0.667 meq/g free amine and 0.656 meq/g amine hydrochloride.

81.8 grams (0.88 moles) of epichlorohydrin were added to the flask by means of the addition funnel and reacted at 80° C. for 5 hours. The reaction mixture was then analyzed and the amine hydrochloride and free amine found to be 2.35% and 1.63% respectively. 3.8 grams (0.04 mole) of additional epichlorohydrin were then added to the flask. After addition of 46 grams of ethanol and 46 grams of water to adjust the solids content, the final analysis was:

| | |
|---|---|
| % Actives (equivalent weight) | 46.0 |
| % Amine Hydrochloride (molecular weight 389.5) | 1.1 |
| % Free Amine (molecular weight 353) | 1.0 |
| % Solids | 50.0 |
| pH, 1% | 5.1 |

EXAMPLE 13

Each of the bis-quaternary ammonium compounds of Examples 8–12 were tested for substantivity as follows:

400 milliliters (ml) of deionized water containing 0.5% by weight of Pyrazol Fast Rubine BLN dye (Sandoz Colors and Chemicals) was prepared and adjusted to a pH of 3.5 with sulfuric acid. 200 ml of 0.0035 mmole/g solutions of each of the bis-quaternary ammonium compounds in deionized water were also prepared.

Six 2-inch square test swatches of standard wool flannel (Test Fabrics, Inc.) were refluxed in ethanol to remove any deposits or oils, and dried.

A test swatch was immersed in the bis-quat aqueous solution to be tested for three minutes, rinsed with warm tap water and wrung damp dry. The thus treated test swatch was then immersed in the Rubine dye aqueous solution, maintained at 100° F. for 5 minutes, then removed, rinsed with warm tap water, wrung damp dry and allowed to dry on a paper towel. The intensity of the color imparted to the test swatch is an indication of the substantivity of the bis-quat compound tested. A control was run substituting water for the bis-quaternary ammonium compound solution. Results are tabulated in Table I

TABLE I

| Bis-Quat, R—Alkyl Group | Observation |
|---|---|
| Control | Light Pink |
| C-1 | Light Pink |
| C-8 | Light Red |
| C-12 | Medium Red |
| C-18 | Dark Red |

TABLE I-continued

| Bis-Quat, R—Alkyl Group | Observation |
|---|---|
| C-22 | Dark Red |

The results of Table I show that the lowest member of bis-quat compounds, i.e., R=methyl in graphic formula II, is not substantive and thus would offer no hair conditioning effect. The octyl homologue, i.e., R=octyl, $R^1$, $R^2$=methyl, is minimally substantive so some conditioning is possible but would be minimal. The lauryl homologue (R=C-12) is more substantive than the octyl homologue. The stearyl (R=C-18) and docosanyl (R=C-22) homologues are very substantive and thus would be very effective hair conditioners.

Although the present invention has been described with reference to specific details of certain embodiments thereof, it is not intended that such details should be regarded as limitations upon the scope of the invention, except as and to tha extent that they are included in the accompanying claims.

I claim:

1. A bis-quaternary ammonium compound represented by the following graphic formula:

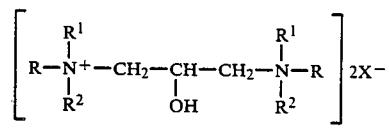

wherein R is a $C_{12}$–$C_{26}$ alkyl, $R^1$ and $R^2$ are the same and are a $C_1$–$C_4$ alkyl, and X is a negative radical selected from the group consisting of Cl, F, Br, $NO_3$, $CH_3SO_3$ and $CH_3C_6H_4SO_3$.

2. The bis-quaternary compound of claim 1 wherein R is a $C_{18}$–$C_{22}$ alkyl, and $R^1$ and $R^2$ are each methyl.

3. The bis-quaternary compound of claim 2 wherein the negative radical X is Cl.

4. 2-hydroxy propylene-1,3-bis(dimethyl lauryl ammonium chloride).

5. 2-hydroxy propylene-1,3-bis(dimethyl stearyl ammonium chloride).

6. 2-hydroxy propylene-1,3-bis(dimethyl docosanyl ammonium chloride).

7. 2-hydroxy propylene-1-dimethyl lauryl-3-dimethyl stearyl ammonium chloride.

* * * * *